US011707051B2

(12) United States Patent
Clarke et al.

(10) Patent No.: US 11,707,051 B2
(45) Date of Patent: Jul. 25, 2023

(54) THERAPEUTIC APPARATUS FOR AN ANIMAL

(71) Applicant: INNOVATIVE PET PRODUCTS PTY LTD, Bundall (AU)

(72) Inventors: Hazel Clarke, Southport (AU); Joseph Clarke, Southport (AU)

(73) Assignee: INNOVATIVE PET PRODUCTS PTY LTD, Bundall (AU)

( * ) Notice: Subject to any disclaimer, the term of this patent is extended or adjusted under 35 U.S.C. 154(b) by 174 days.

(21) Appl. No.: 16/633,791

(22) PCT Filed: Jul. 24, 2018

(86) PCT No.: PCT/AU2018/050767
§ 371 (c)(1),
(2) Date: Jan. 24, 2020

(87) PCT Pub. No.: WO2019/018887
PCT Pub. Date: Jan. 31, 2019

(65) Prior Publication Data
US 2020/0196566 A1   Jun. 25, 2020

(30) Foreign Application Priority Data

Jul. 27, 2017 (AU) ................................ 2017902963

(51) Int. Cl.
*A01K 5/00* (2006.01)
*A01K 15/02* (2006.01)
(Continued)

(52) U.S. Cl.
CPC .............. *A01K 5/00* (2013.01); *A01K 15/026* (2013.01); *A61M 21/02* (2013.01); *A61M 2021/0022* (2013.01); *A61M 2250/00* (2013.01)

(58) Field of Classification Search
CPC .. A01K 15/026; A01K 5/0114; A01K 5/0135; A01K 5/0142; A01K 15/025; A01K 5/01
See application file for complete search history.

(56) References Cited

U.S. PATENT DOCUMENTS 85,342,258     9/2013  Vermeegen
9,402,370 B2 * 8/2016  Lindskov ............. A01K 5/0114
(Continued)

FOREIGN PATENT DOCUMENTS

CN    204653331 U    9/2015
CN    204653332 U    9/2015
(Continued)

OTHER PUBLICATIONS

International Search Report and Written Opinion mailed in PCT/AU2018/050767 dated Aug. 23, 2018.
(Continued)

*Primary Examiner* — Trinh T Nguyen
(74) *Attorney, Agent, or Firm* — Wissing Miller LLP (57) ABSTRACT

There is provided a therapeutic apparatus for an animal, the apparatus comprising a base and a plurality of food entrapment members that extend from the base, the food entrapment members and the base being configured so that, together, they define zones in which food paste can be trapped so that a tongue of a pet is inhibited from licking the food paste out of the zones, the base and the entrapment member being of a food grade material, in which the entrapment members extend from a first side of the base.

21 Claims, 9 Drawing Sheets

(51) Int. Cl.
*A61M 21/02* (2006.01)
*A61M 21/00* (2006.01)

(56) References Cited

U.S. PATENT DOCUMENTS

| | | | |
|---|---|---|---|
| 10,172,323 B2* | 1/2019 | Glinsky | A01K 5/0275 |
| 2006/0005774 A1* | 1/2006 | Newman Bornhofen | ............... |
| | | | A01K 5/0135 |
| | | | 119/61.5 |
| 2006/0213447 A1* | 9/2006 | Kitchen | A01K 5/0114 |
| | | | 119/61.5 |
| 2009/0126641 A1* | 5/2009 | Anderson | A01K 5/0114 |
| | | | 119/61.5 |
| 2011/0308470 A1 | 12/2011 | Vermeegen | |
| 2013/0305996 A1 | 11/2013 | Lindskov | |
| 2014/0060442 A1 | 3/2014 | Resseman | |
| 2014/0158054 A1* | 6/2014 | Clarke | A01K 5/00 |
| | | | 119/51.01 |
| 2017/0071155 A1 | 3/2017 | Gailen | |

FOREIGN PATENT DOCUMENTS

| | | |
|---|---|---|
| CN | 204653333 U | 9/2015 |
| GB | 2410409 | 8/2005 |
| WO | 2011032285 | 3/2011 |
| WO | 20130086581 | 6/2013 |
| WO | 2013156033 | 10/2013 |
| WO | 20130156033 | 10/2013 |
| WO | 20160105443 | 6/2016 |

OTHER PUBLICATIONS

Supplementary EP Search Report mailed in EP 18838352.5 dated Mar. 22, 2021 (7 pages).
Chinese Search Report dated Jul. 18, 2021 in corresponding Chinese Application No. 2018800585242 (3 pgs.) (Note: an English language translation of the Search Report is not available online, including in the Global Dossier and after reasonable attempts, Applicant has been unable to generate a machine translation).
Chinese Office Action dated Jul. 26, 2021 in corresponding Chinese Application No. 2018800585242 (4 pgs.).

* cited by examiner

THERAPEUTIC APPARATUS FOR AN ANIMAL

CROSS-REFERENCE TO RELATED APPLICATIONS

This application is a 371 of PCT/AU2018/050767 filed on Jul. 24, 2018, published on Jan. 31, 2019 under publication number WO 2019/018887, which claims priority benefits from Australian Patent Application No. 2017902963 filed on Jul. 27, 2017, the disclosure of each is incorporated herein in their entirety by reference.

FIELD

Various examples of a therapeutic apparatus for an animal are described herein.

BACKGROUND

Pet behavioural problems can arise when pets become bored or suffer from separation anxiety. This can happen when pets are left alone for extended periods. Because of the boredom and/or separation anxiety, pets can exhibit destructive behaviour.

It is known that a pet's environment can be enriched with toys and treats. However, it can be a challenge to provide edible treats to pets for extended periods of time and with a minimum of calorific input.

SUMMARY

According to one aspect there is provided a therapeutic apparatus for an animal, the apparatus comprising:
a base; and
a plurality of food entrapment members that extend from the base, the food entrapment members and the base being configured so that, together, they define zones in which food paste can be trapped so that a tongue of a pet is inhibited from licking the food paste out of the zones, the base and the entrapment member being of a food grade material, in which the entrapment members extend from a first side of the base and the base at least partially encloses a volume to have an internal surface from which the food entrapment members extend into the volume.

The base may be rectangular.

A wall may be arranged on the base to extend around a licking region in which the food entrapment members are arranged.

Upper ends of the food entrapment members may be approximately aligned with an upper edge of the wall.

A second side of the base may be a surface that is configured to inhibit skidding of the base while the first side is licked.

Skidding of the apparatus may be inhibited by inclusion of a suction device on the second side of the apparatus.

The enclosed volume may be a passage that extends through the base.

The passage may be frustoconical.

The material of the base may be resilient and the base and entrapment members may be configured so that the base can be inverted to present the internal surface externally.

The suction device may substantially close at least one end of the passage.

The food entrapment members may be an array of discrete projections. The discrete projections may be evenly spaced.

The projections may be posts or rods that extend from the base. Each rod may be cylindrical and may have a rounded upper or free end.

The food entrapment members may each be two intersecting catch members. The catch members may be generally straight. The catch members may intersect substantially orthogonally.

The food entrapment members may define an array of discrete pockets in which the food paste can be trapped.

The entrapment members may be in the form of intersecting ridges.

The base may have a second, frustoconical side.

According to another aspect there is provided a therapeutic apparatus for an animal, the apparatus comprising:
a base; and
a plurality of food entrapment members that extend from the base, the food entrapment members and the base being configured so that, together, they define zones in which food paste can be trapped so that a tongue of a pet is inhibited from licking the food paste out of the zones, the base and the entrapment member being of a food grade material, in which the food entrapment members are an array of discrete projections and are each two intersecting catch members.

The base may be rectangular and generally flat.

The entrapment members may extend from an upper side of the base.

A wall may be arranged on the base to extend around a licking region in which the food entrapment members are arranged.

Upper ends of the food entrapment members may be approximately aligned with an upper edge of the wall.

A lower side of the base may be a surface that is configured to inhibit skidding of the base while the upper side is licked.

Skidding of the apparatus may be inhibited or prevented by inclusion of a suction device on the lower side.

The catch members may be generally straight. The catch members may intersect substantially orthogonally.

Each two intersecting catch members may connect to an adjacent two intersecting catch members to form a matrix of substantially uniform quadrilateral zones.

The upper side of the base may include a peripheral channel between the wall and the licking region.

DETAILED DESCRIPTION

Figure 1:
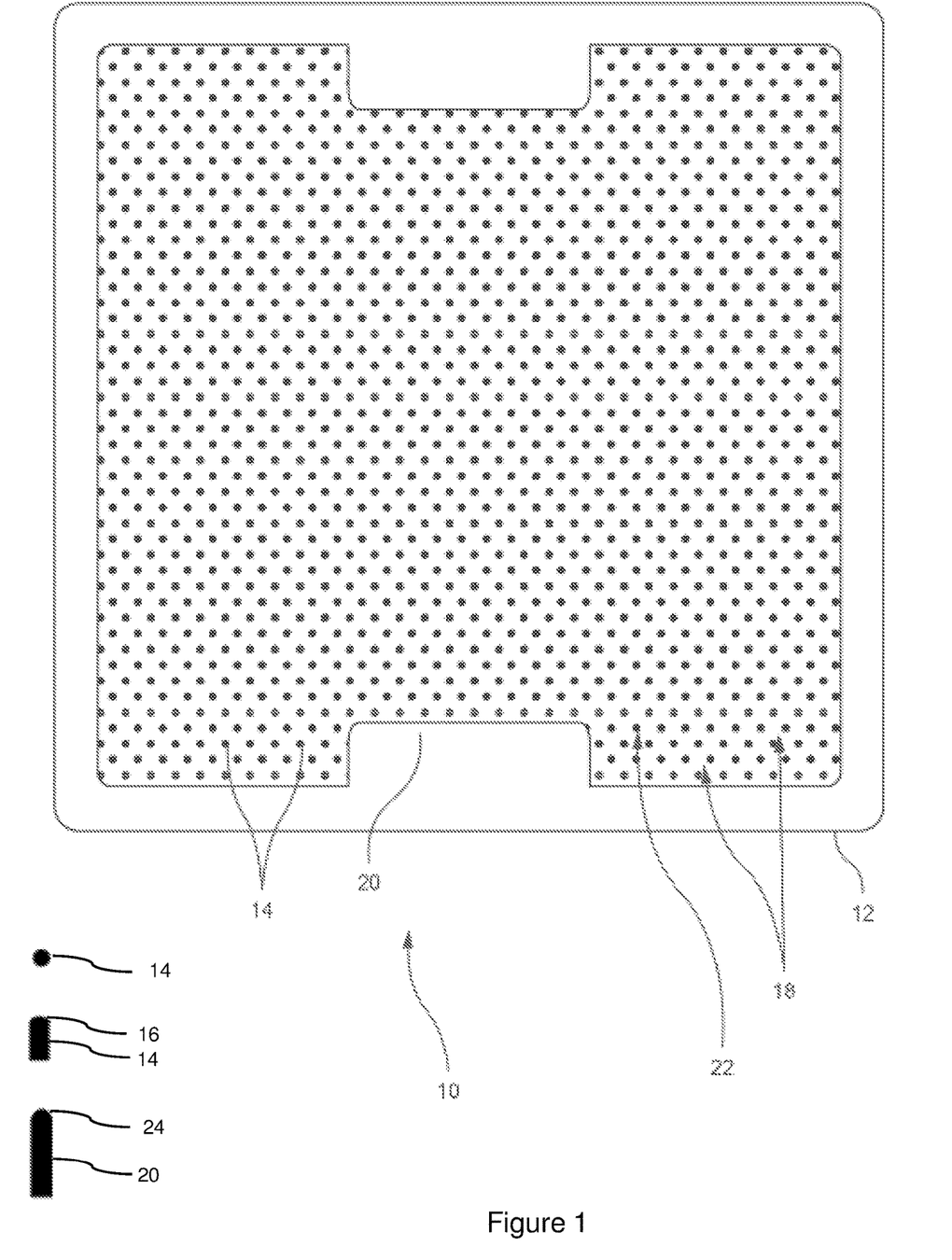
FIG. 1 shows a plan view of one example of a therapeutic apparatus for an animal, including details of projections and a wall that extend from a base of the apparatus.

In FIG. 1, reference numeral 10 generally indicates a therapeutic apparatus for an animal.

The apparatus 10 includes a base 12. The base 12 is rectangular and generally flat. In one example, the base 12 is square. A plurality of food entrapment members extends from the base 12. The food entrapment members, in this example, are an array of discrete projections 14. The projections 14 are evenly spaced across the mat. The projections 14 are posts or rods that extend from the base 12. The projections 14 are cylindrical. The projections 14 have rounded upper ends 16.

The dimensions and spacing of the projections 14 are selected so that they can define zones 18 in which food paste can be trapped so that a tongue of a pet is inhibited from licking the food paste out of the zones 18. "Food paste" means any food that is in a condition in which it can be smeared or pasted into a receptacle such as one of the zones 18. Thus, the food paste can be minced, ground or softened meat and/or vegetables, conventional tinned or canned dog or cat food, or any other form of animal food in a paste-like condition. It is envisaged that the food paste can be smooth or can contain chunks of food elements.

The apparatus 10 can be formed of a food grade material. The food grade material can be a food grade thermoplastic rubber. Such material is BPA-free and is suitable for long term food contact. Thus, the base 12 and the projections 14 are of the food grade material. It is envisaged that other types of material can be suitable, provided that they are safe for long-term animal use.

The projections 14 can have a height of between approximately 1 mm and 3 mm, for example, approximately 2 mm. The base 12 can have a thickness of between approximately 1 mm and 3 mm, for example, approximately 2 mm.

An outside wall 20 extends from the base 12, inwardly from a periphery of the base 12, around a licking region 22. The projections 14 are positioned in the licking region 22. The upper ends 16 of the projections 14 are approximately aligned with an upper edge 24 of the wall 20. Thus, the food paste can be retained within the licking region 22 by the wall 20 to inhibit the food paste from being licked out of the region 22.

The outside wall 20 has a height of between approximately 1 mm and 3 mm, for example, 2 mm.

The outside wall 20 has a rounded upper edge 24.

The apparatus 10 can be provided in various sizes. In one example, the base 12 can be square with sides approximately 20 cm long. However, it is envisaged that other dimensions can also be suitable depending on requirements. For example, for larger dogs, the base can be between approximately 20 cm and 30 cm wide, for example, approximately 25 cm wide, and between approximately 30 cm and 40 cm wide, for example, approximately 35 cm wide.

Figure 2:
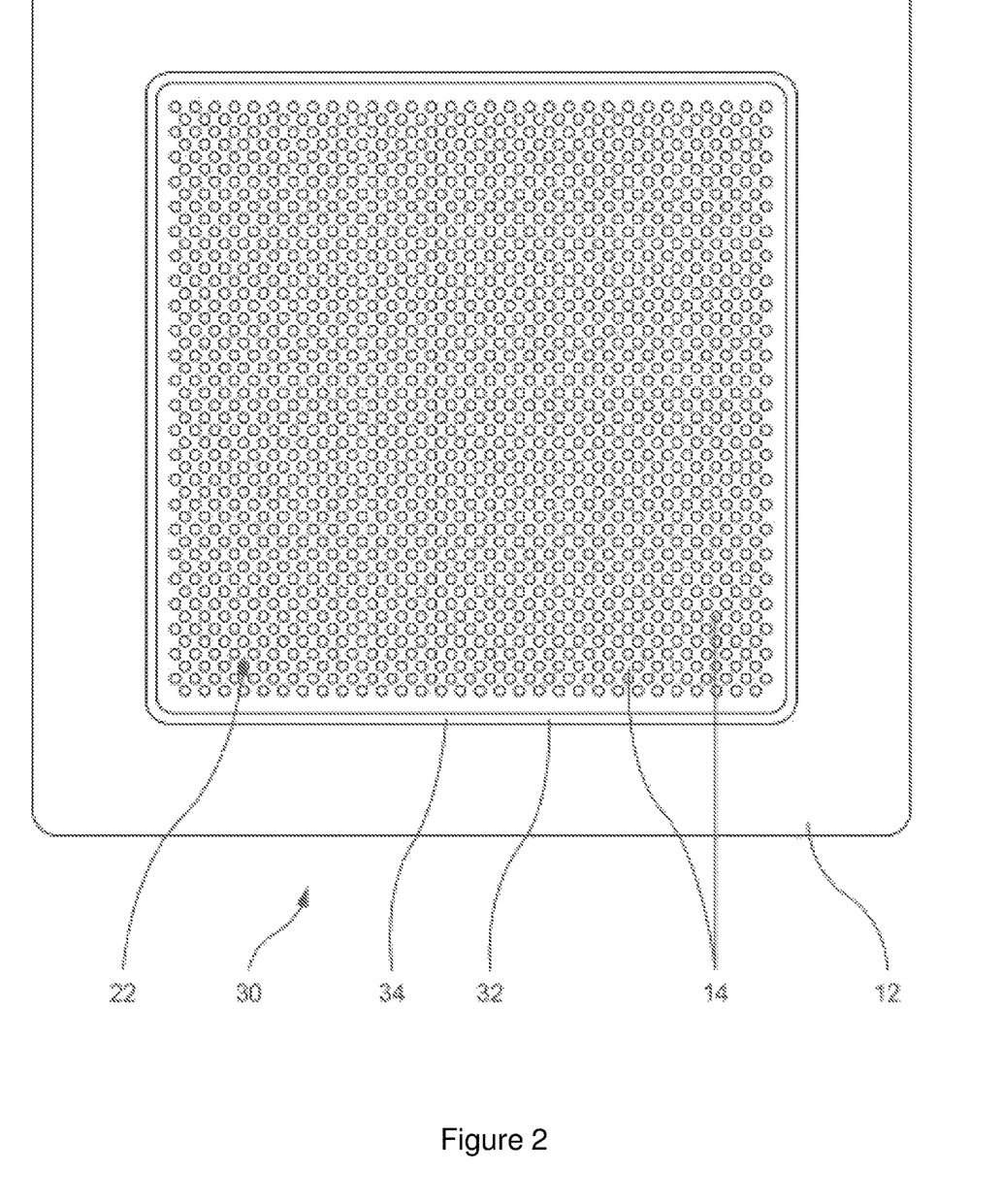
FIG. 2 shows a plan view of another example of a therapeutic apparatus for an animal.

In FIG. 2, reference numeral 30 generally indicates a therapeutic apparatus for an animal.

The therapeutic apparatus 30 includes a wall 32 that extends around the licking region 22, inwardly of a periphery of the base 12. The wall 32 has a rounded upper edge 34.

Figure 3:
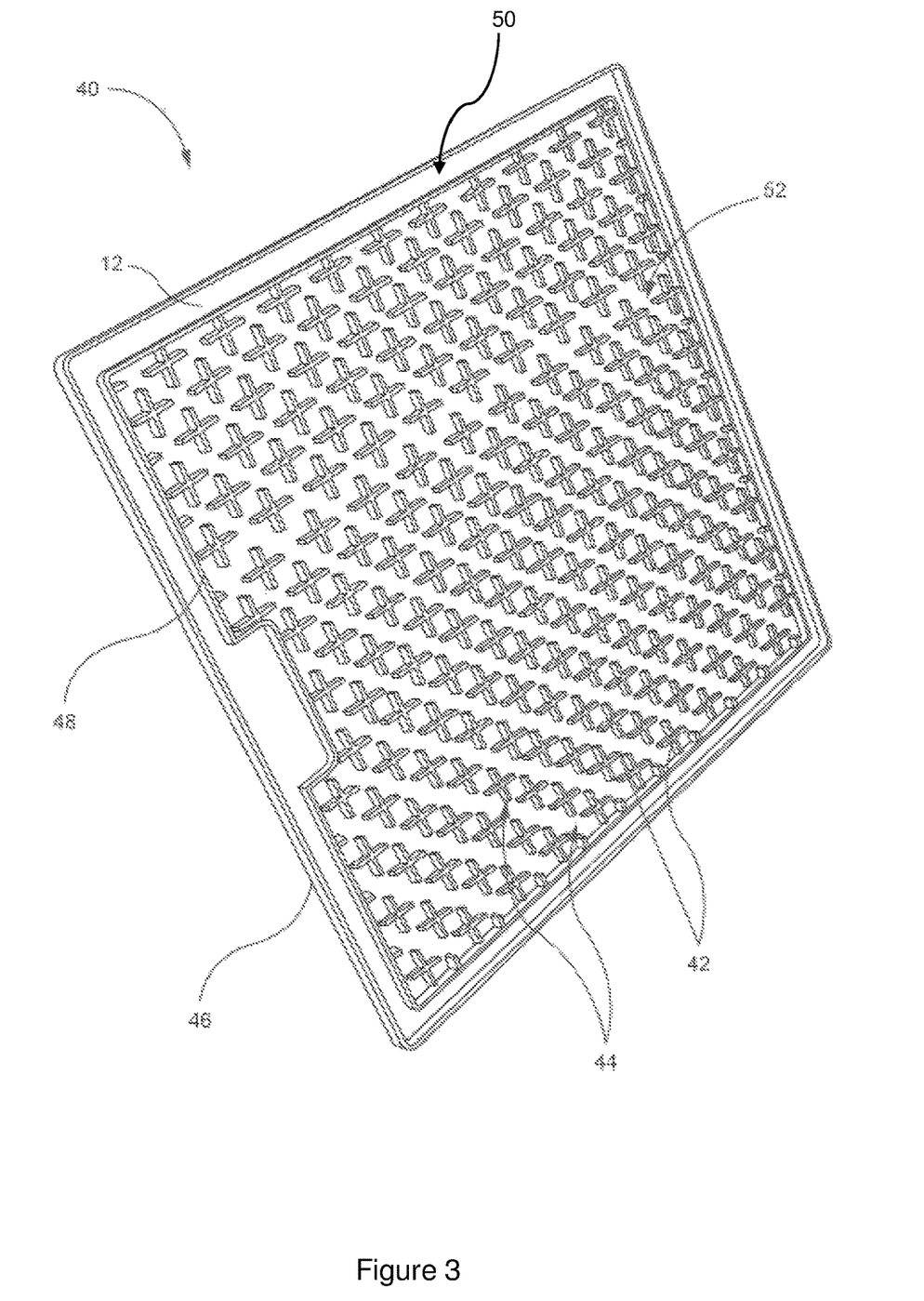
FIG. 3 shows a three-dimensional view, from above, of another example of a therapeutic apparatus for animal.

In FIG. 3, reference numeral 40 generally indicates a therapeutic apparatus for an animal.

The apparatus 40 includes a plurality of food entrapment members in the form of discrete pairs of intersecting catch members 42. The catch members 42 are generally straight. However, it is envisaged that catch members having a different configuration could also be suitable. For example, the catch members 42 could be curved or angular sections.

In this example, the catch members 42 are in form of straight wall sections that intersect each other orthogonally. Thus, the entrapment members in this example are cruciform. It is envisaged that the wall sections could intersect at different angles.

The entrapment members are evenly spaced and define zones 44 in which the food paste can be trapped.

In this example, an outer wall 46 extends from a periphery of the base 12. An inner wall 48 also extends from the base 12, inwardly of the outer wall 46. Thus, a channel 50 is formed by the walls 46, 48 about a licking region 52. The channel 50 can be filled with water to inhibit ants and other insects from gaining access to the food paste.

The entrapment members extend from the base 12 in the licking region 52. The walls 46, 48 have a height of between approximately 1 mm and 3 mm, for example, approximately 2 mm. Upper edges of the walls 46, 48 can be rounded. The catch members 42 have a height of between approximately 1 mm and 3 mm, for example, approximately 2 mm.

Each of four arms of each entrapment member defined by the intersecting walls 46, 48 have a length of between approximately 5 mm and 10 mm. Points of intersection of the walls 46, 48 can be spaced between approximately 5 mm to 10 mm from each other.

The apparatus 40 is particularly suited for retaining thick and sticky treats such as peanut butter or soggy biscuits.

Figure 4:
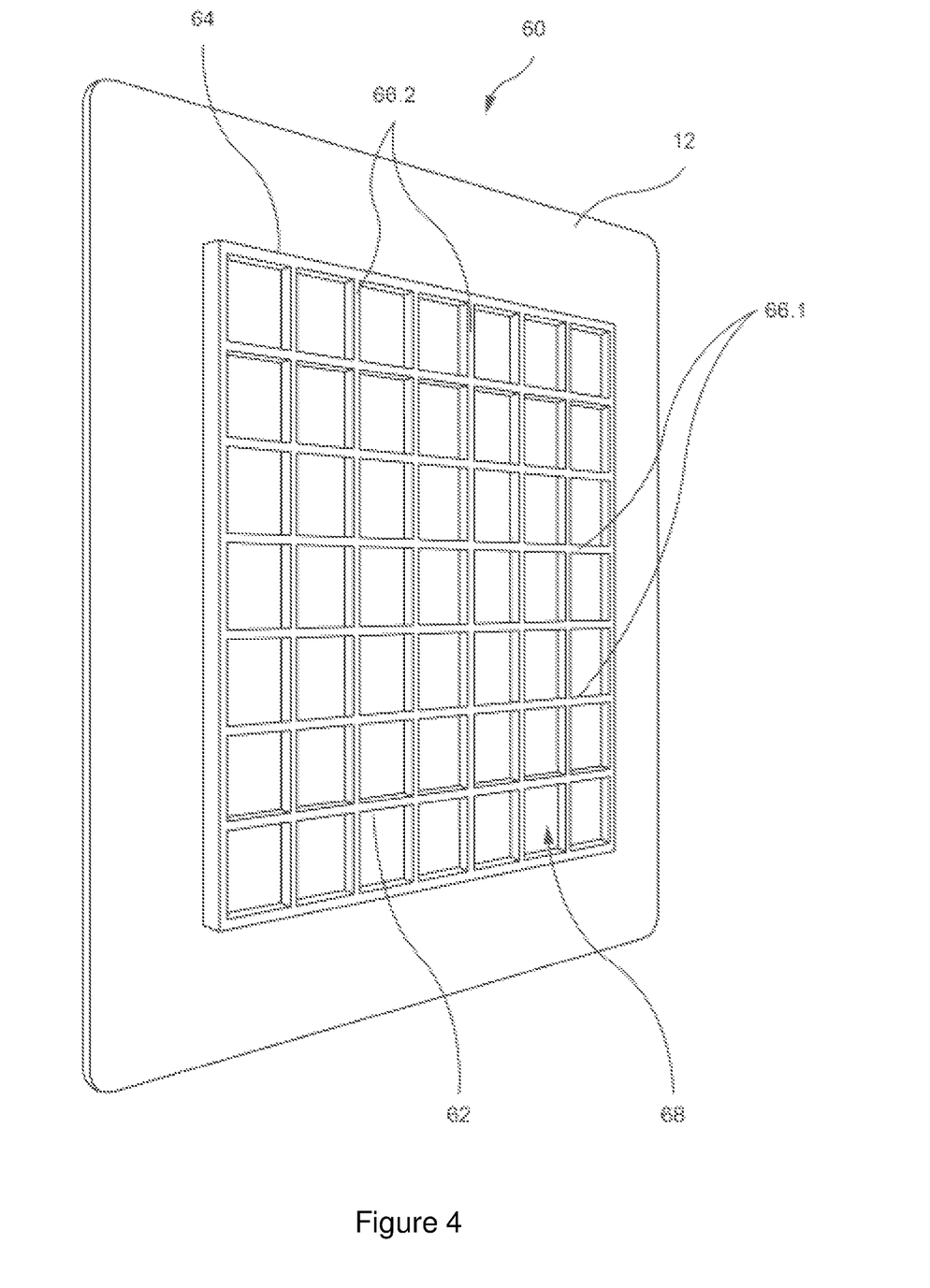
FIG. 4 shows a three-dimensional view, from above, of another example of a therapeutic apparatus for an animal.

In FIG. 4, reference numeral 60 generally indicates a therapeutic apparatus for an animal.

The apparatus 60 includes a plurality of entrapment members in the form of an array of rectangular or square catch members 62 arranged in a rectangular or square grid on the base 12. The catch members 62 are provided by a rectangular or square outer wall 64 with two sets of intersecting inner walls 66.1, 66.2, each set extending between respective opposed sections of the wall 64. Thus, the base 12 and the catch members 62 define regions or pockets 68 in which the food paste is trapped.

The outer wall 64 is positioned inwardly of a periphery of the mat 12.

The walls 64, 66 have a height of between approximately 1 mm and 3 mm, for example, approximately 2 mm.

Each pocket 68 has sides between approximately 15 mm and 25 mm long. The length would depend on the size of the animal.

The apparatus 60 is particularly suited for trapping chunky food paste such as crushed meat or fish.

Figure 5:
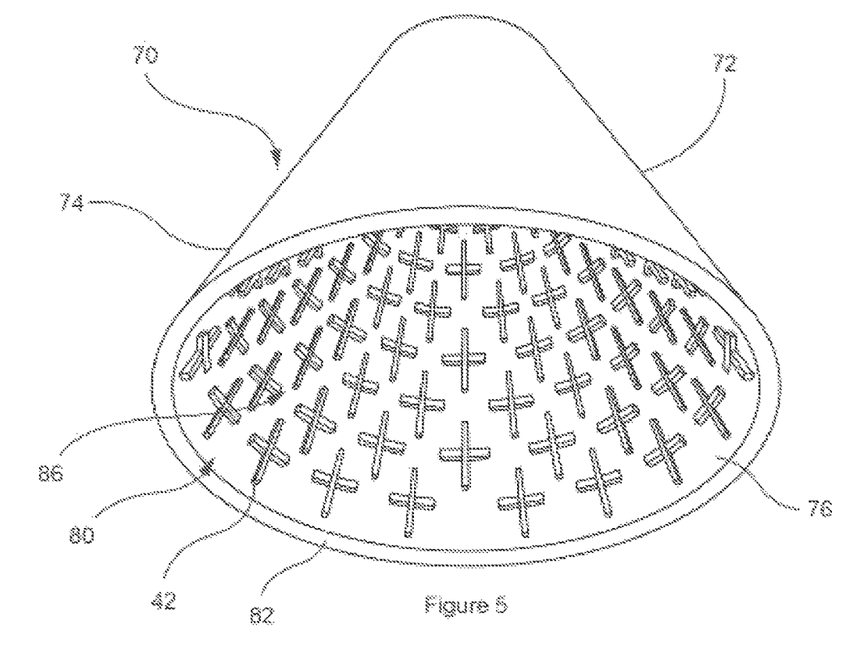
FIG. 5 shows a three-dimensional view of another example of a therapeutic apparatus for an animal.
Figure 6:
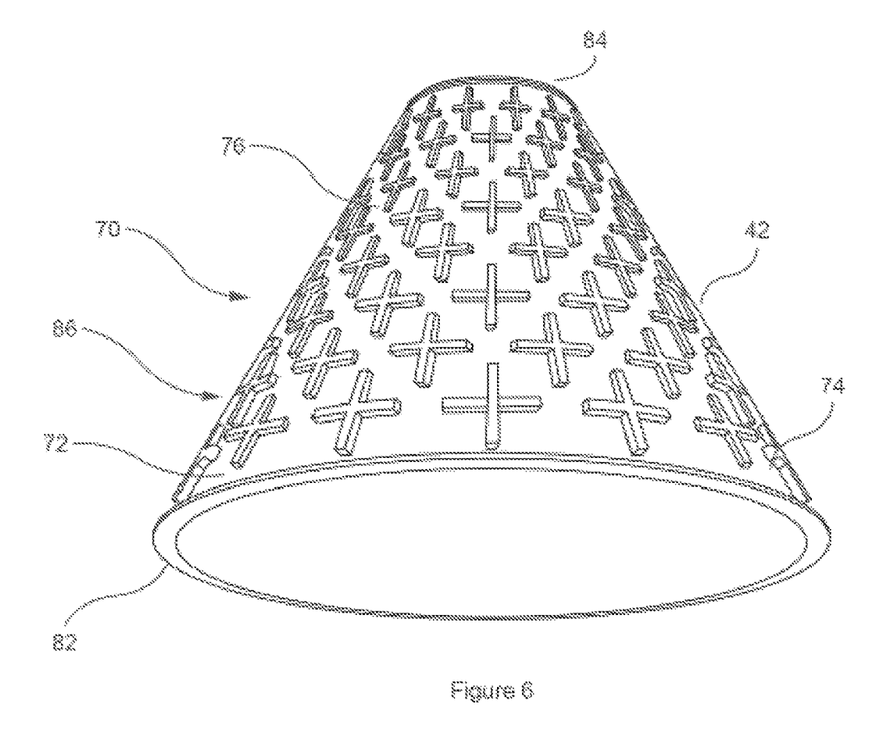
FIG. 6 shows a three-dimensional view of the apparatus of FIG. 5 in an inverted configuration.

In FIGS. 5 and 6, reference numeral 70 generally indicates a therapeutic apparatus for an animal.

The apparatus 70 includes a base 72 having a frustoconical wall 74 that has an inner side 76 that defines a frustoconical passage 80. The wall 74 has an outer side 77 that is frustoconical.

Any of the entrapment members described above can be positioned on the inner side 76 to extend into the passage 80. In the example shown in FIGS. 5 and 6, the entrapment members are like those of the apparatus 40 and so are indicated with reference numeral 42.

A peripheral major wall 82 extends from a major end of the inner side 76. A peripheral minor wall 84 extends from a minor end of the inner side 76. Thus, a frustro conical licking region 86 is located or arranged between the walls 82, 84.

The height of the walls 82, 84 is between approximately 1 mm and 3 mm, for example, approximately 2 mm.

As set out above, the base 12 and the entrapment members can be of a thermoplastic rubber. Such material is resiliently flexible. Thus, the apparatus 70, as shown in its operative configuration, in FIG. 5, can be inverted for cleaning purposes and for the application of the food paste, into the configuration shown in FIG. 6.

The apparatus 70 is useful in that it will tumble around as the animal attempts to lick the food paste from the licking region 86. This can engage the animal in a diversionary manner because the animal may attempt to hold onto the apparatus 70 while licking.

Furthermore, the apparatus 70 is generally frustoconical. It follows that it will tend to roll back to the animal, which will help to avoid the apparatus from being lost. This will also help to avoid frustrating the animal.

In this example, the apparatus 70 can have a length of between approximately 10 cm and 15 cm, for example between approximately 11 cm and 13 cm. A major end of the apparatus can have a diameter of between approximately 12 cm and 20 cm, for example between approximately 14 cm and 18 cm. A minor end of the apparatus can have a diameter of between approximately 3 cm and 12 cm, for example between 5 cm and 9 cm. Various other dimensions could also be suitable depending on the size of the animal and other parameters.

In the various examples described, the apparatus can be a unitary, one-piece article. For example, the apparatus can be moulded from the material, for example, the thermoplastic rubber or some other animal food grade material. It is envisaged that other forms of fabrication can be used.

The apparatus 70 has been described as frustoconical. It is envisaged that the therapeutic apparatus can be many different shapes. Irrespective of the shape, the therapeutic apparatus can be inverted or turned inside-out to allow for cleaning or the application of the food paste before being reversed back into its operative condition, or can be used in the inverted configuration.

In one example, the apparatus is generally tubular, with the frustoconical shape being a species. In those examples, the apparatus can be between 12 and 20 cm long. It is envisaged that other dimensions may also be suitable.

Figure 7:
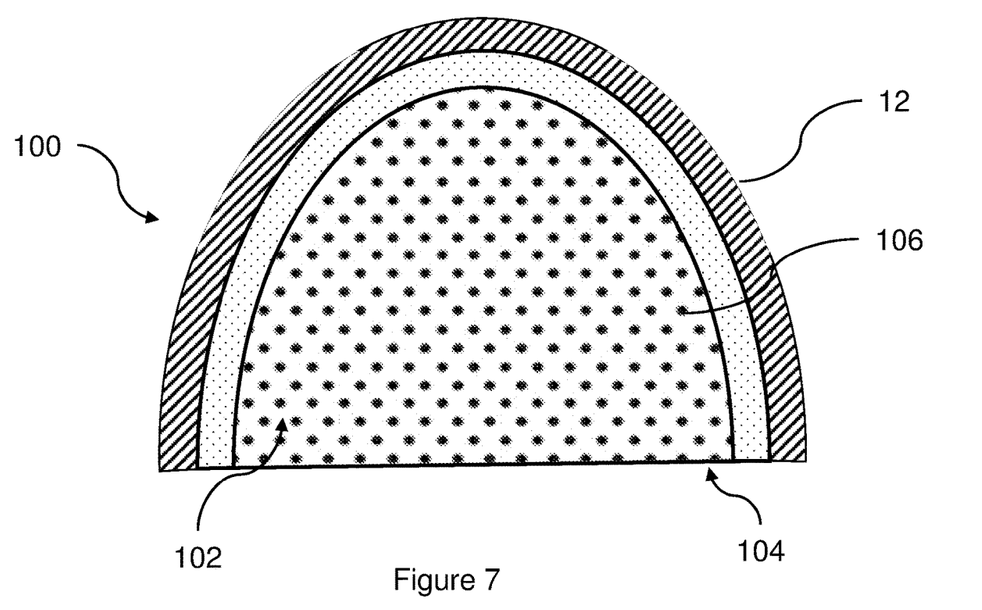
FIG. 7 shows a sectioned view of another example of a therapeutic apparatus for an animal.
Figure 8:
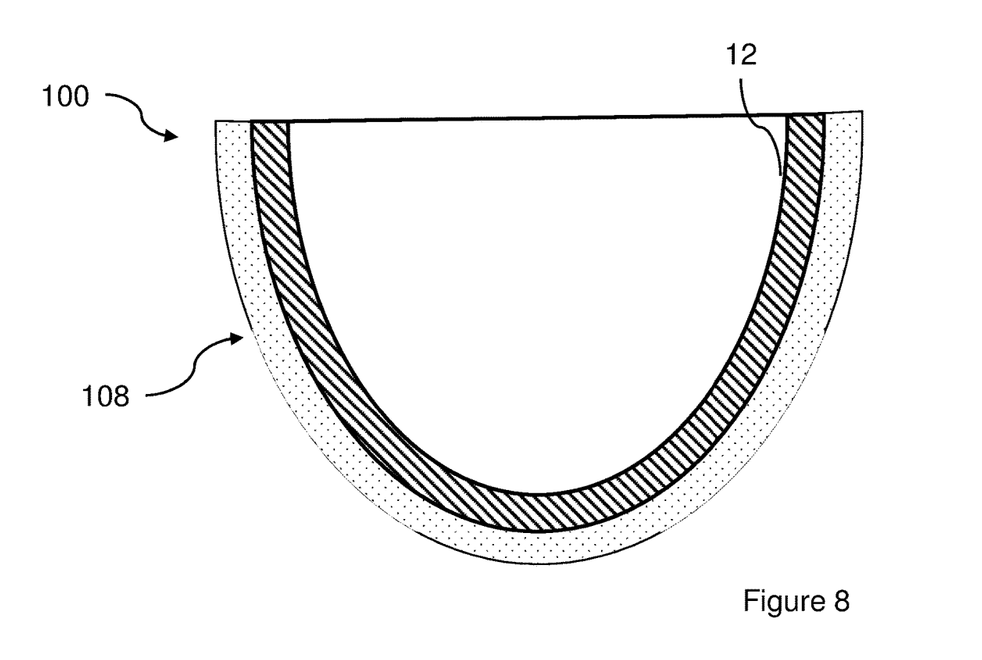
FIG. 8 shows a sectioned view of the apparatus of FIG. 7, in an inverted configuration.

In FIGS. 7 and 8, reference numeral 100 generally indicates another example of a therapeutic apparatus for an animal.

The apparatus 100 is shown to illustrate that the base 12 need not define a passage. The base may be any configuration that provides an unstable bearing surface. Here, the base 12 defines a partially enclosed part-ellipsoidal (bowl-shaped) volume 102 that is accessible from a mouth 104. Food entrapment members 106 extend from the base 12 into the volume 102. The food entrapment members 106 can be in the form of any of the various types of food entrapment members described above or can be in the form of other food entrapment members.

The base 12 is of an elastomeric material and can be inverted into the condition shown in FIG. 8. This provides ready access to the members 106, which are also generally indicated at a licking region 108. In that condition, the licking region 108 can be cleaned and/or smeared or covered with the food paste. Once that is done, the base 12 can be returned to the condition shown in FIG. 7.

Thus, the base 12 can be configured so that, when inverted, it can retain the shape shown in FIG. 8.

Figures 9, 10:
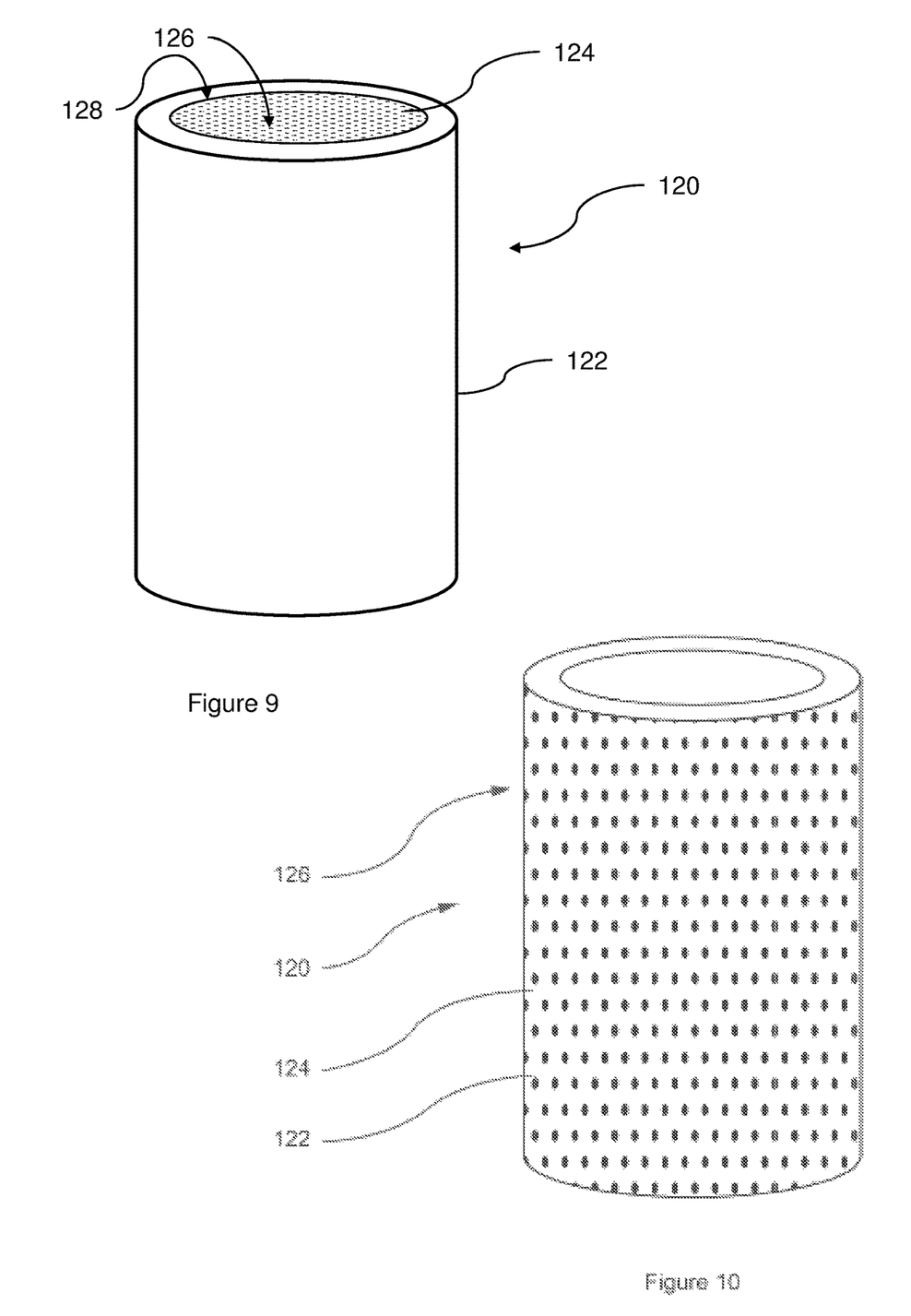
FIG. 9 shows a three-dimensional view of another example of a therapeutic apparatus for an animal.
FIG. 10 shows the apparatus of FIG. 9, in an inverted configuration.
Figure 11:
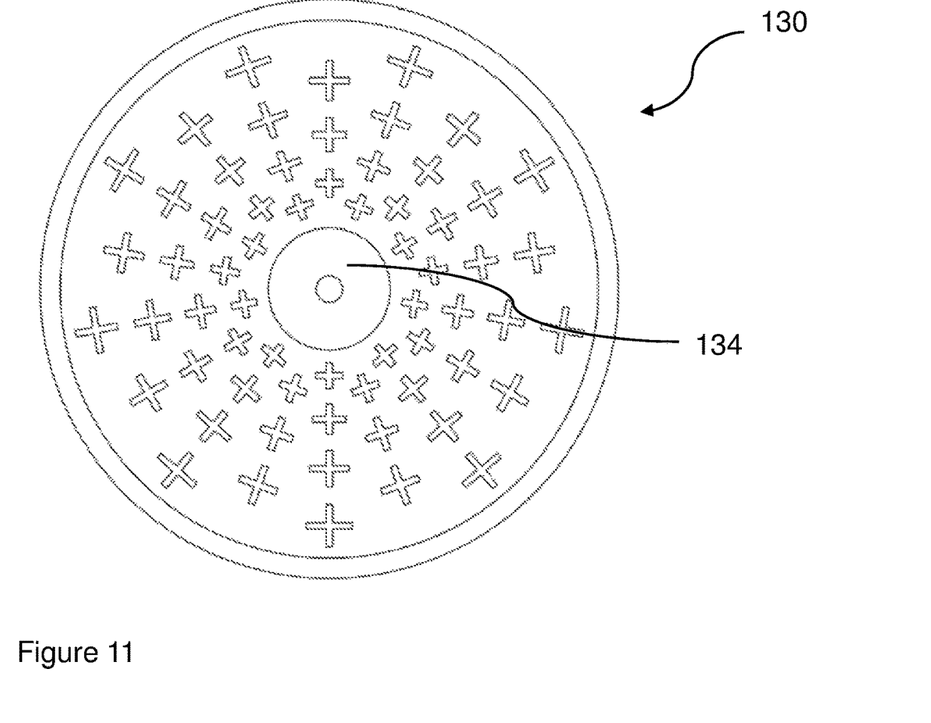
FIG. 11 shows a view from above of another example of a therapeutic apparatus for an animal.
Figure 12:
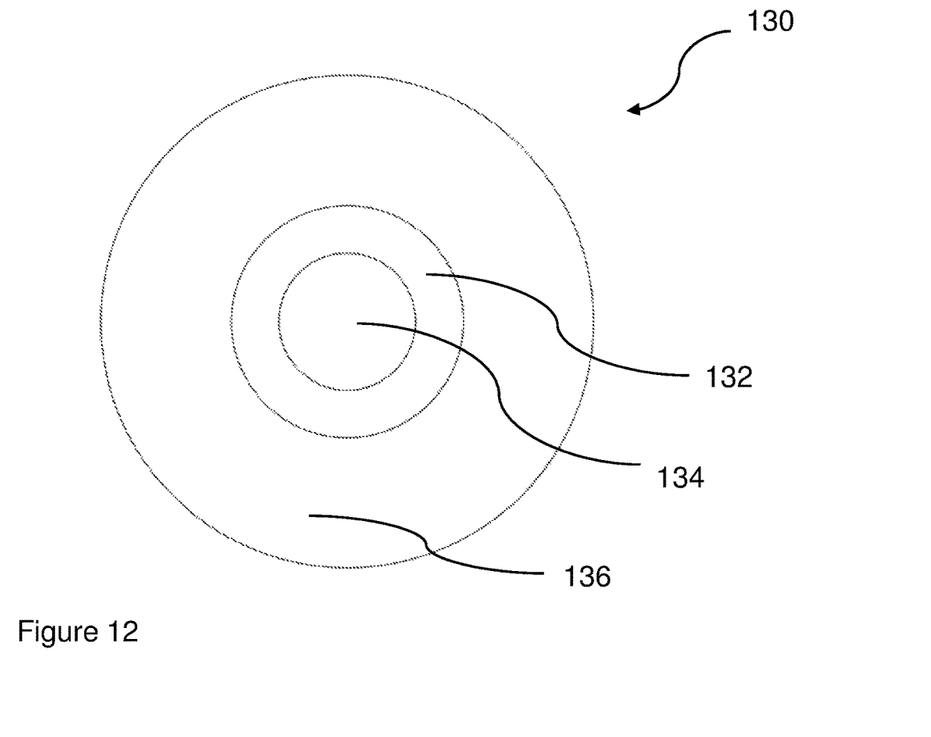
FIG. 12 shows a view from below of the apparatus of FIG. 11.
Figure 13:
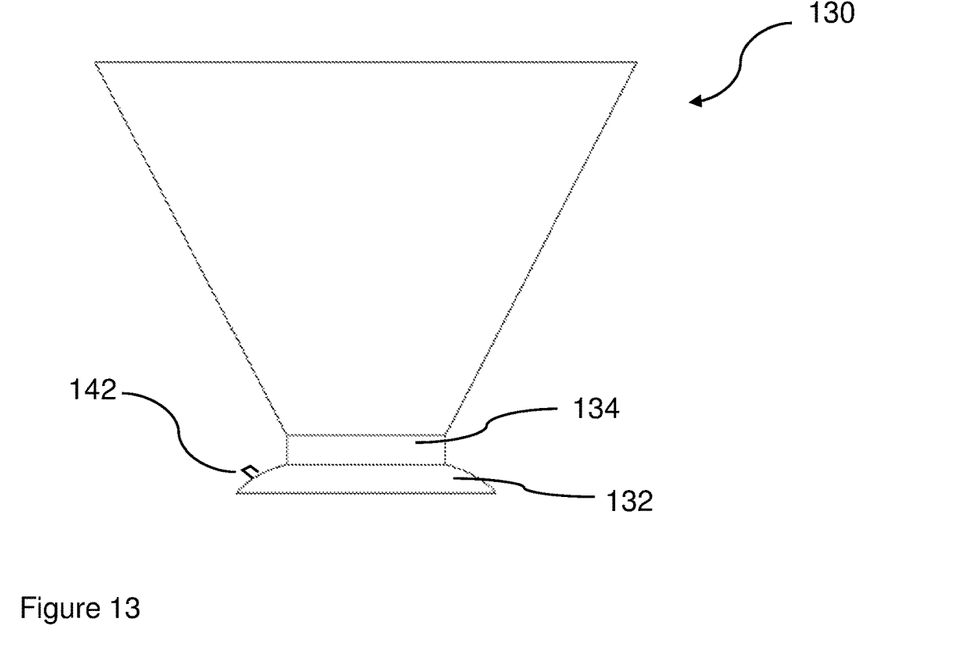
FIG. 13 shows a side view of the apparatus of FIG. 11.
Figure 14:
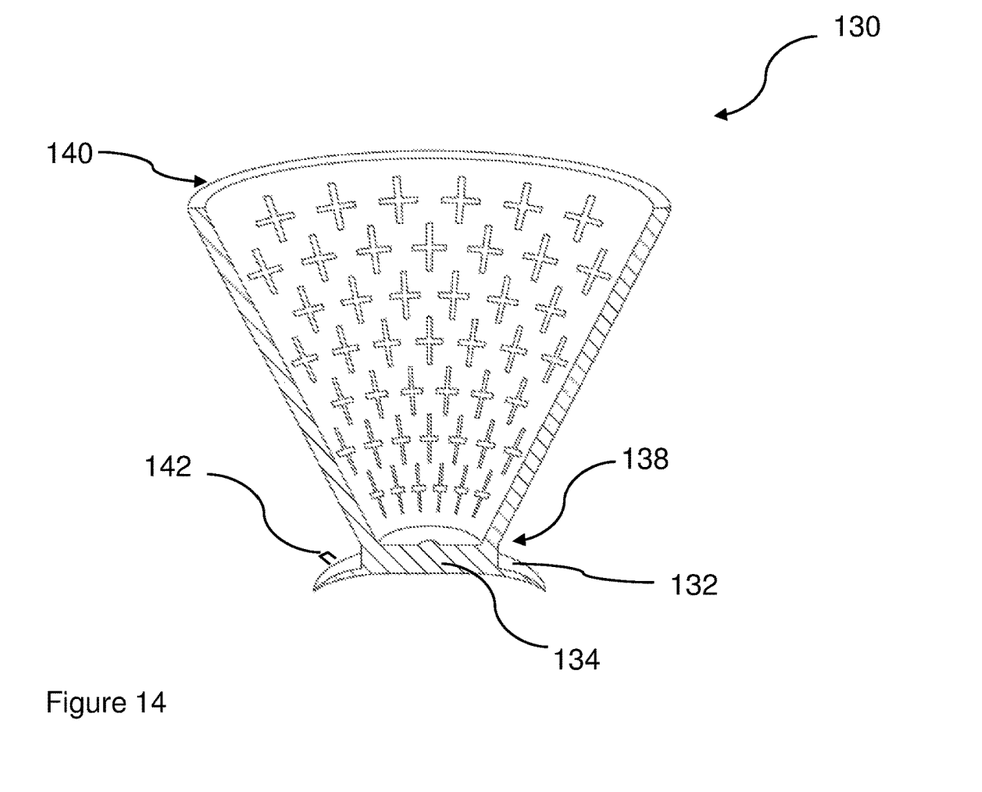
FIG. 14 shows a sectioned view of the apparatus of FIG. 11.

In FIGS. 9 and 10, reference numeral 120 generally indicates an example of a therapeutic apparatus for an animal.

In this example, the apparatus has a base in the form of a tubular wall 122. The wall 122 is made of the same or similar material to that of the other apparatus described above. The wall 122 is also of a thickness and length that allows it to be turned inside out or inverted into the condition shown in FIG. 10.

The entrapment members of any one of the apparatus described above are positioned on an internal surface 124 to provide an internal licking region 126.

The wall 122 can have a length of between approximately 10 cm to 22 cm, for example between approximately 12 cm and 20 cm. Other lengths can also be suitable, depending on the animal. The type of animal can also determine a diameter of a passage 128 defined by the wall 122.

In any of the examples of the apparatus of the invention, skidding or sliding of the apparatus may be prevented or inhibited by inclusion of a suction device onto the apparatus. Where the apparatus of the invention has a flat configuration, as illustrated in for example FIGS. 1 to 4, the suction device may be attached or affixed to the lower side of the apparatus, in contact with the surface upon which the apparatus is intended to rest.

The suction device may be affixed in any practicable manner to an apparatus of the invention, and may be permanently affixed or removably affixed. He suction device may also be integrally manufactured with the apparatus as a unitary piece.

A suction device included in an example of the apparatus 130 which has an enclosed configuration is shown in FIGS. 11 to 14. In this example, the suction device is a suction cup 132 attached to a foot 134 which effectively covers the minor end 138 of the frustoconically shaped apparatus 130. In this way, the apparatus 130 may be reversibly attached to a surface to prevent or minimise slipping or skidding of the apparatus when in use.

The foot 134 and suction cup 132 can be manufactured in parts or as a unitary part, and can be attached to the wall 136 at the minor end 138 of the frustoconically shaped apparatus or the major end 140, but preferably the minor end 138. Alternatively, the apparatus 130 is manufactured as a unitary piece including the foot 134 and suction cup 132.

A user will appreciate that downward pressure on the apparatus 130 towards a surface with which the suction cup 132 is in contact, will cause the suction cup 132 to suctionally secure to the surface and thereby releasably secure the apparatus 130 to the surface.

The suction cup 132 may include an outwardly projecting tab 142, which may be taken up by hand and used to pry the suction cup 132 away from the surface to release the suction grip of the suction cup 132 relative to the surface.

This configuration of the apparatus of the invention is particularly useful when it is desired to attend to an animal and distraction is required. This configuration remains in one position when suctioned to a surface, keeping the animal in one location and preoccupied while being attended to. In addition, the attention can be washing of the animal as this configuration also prevents wetting of the food on the inner side 76 while washing the animal.

In use, a food paste can be spread into the licking region and into the zones defined by the various entrapment members. An animal, for example a dog or cat, can lick the licking region for an extended length of time without being able to remove all the food paste.

The therapeutic apparatus described above is a challenge/reward-based treat delivery device that is capable of engaging pets over extended periods while delivering small amounts of a treat in the form of the food paste referred to above.

Licking has been recognised as promoting a state of calm in dogs. Thus, the use of the various apparatus described herein can offer a calming distraction to a dog while the dog is alone or is suffering from a stressful experience such as a thunderstorm or fireworks.

It is submitted that the apparatus described above provide a tactile challenge in that the food paste is inhibited from being released to the animal by the various entrapment members. Thus, the apparatus can inhibit "over-treating" that is often associated with food-based diversion therapies.

In various pets, such as dogs, the buccal cavity, namely, the lips, tongue and mouth, are a major centre of thermoregulation. In use, the apparatus can be frozen in summer for providing a cooling effect to pets as they lick the apparatus. Thus, the material of the apparatus can be selected to be freezer-safe.

The apparatus can help to promote oral health because extended licking promotes a reduction in bacteria and undigested food particles from the tongue ('*Tongue-cleaning methods: a comparative clinical trial*'—Pedrazzi Vl, Sato S, de Mattos Mda G, Lara E H, Panzeri H.) It is submitted that the lingual stimulation also stimulates saliva production that helps clean the tongue teeth and gums.

The material of the apparatus is selected so that it can be hand washed repeatedly without damage.

Various tests carried out on the apparatus indicate that the apparatus is acceptable to pets. Generally, the entrapment members are effective in trapping small food particles and so increase the length of time the pet spends licking the apparatus in an attempt to gain access to the food. This extended period of licking delivers diversion and oral benefits referred to above.

In the case of the apparatus 70 and 100, there is provided a device that can further engage the animal because the apparatus 70, 100 will tend to roll or tumble about as it is licked. To lick effectively, the animal will have to find a way to trap the apparatus 70, 100 such as by holding the apparatus 70, 100 between its paws.

The appended claims are to be considered as incorporated into the above description.

In the above description, the use of common reference numerals in different examples is for convenience only and is intended to refer to similar components and not necessarily identical components. Furthermore, where practical, it is envisaged that similar components in respective examples can be interchanged to provide further examples. It is submitted that such further examples would be apparent to a person skilled in the art and it is therefore not necessary to describe such further examples in any detail.

Throughout the specification, including the claims, where the context permits, the term "comprising" and variants thereof such as "comprise" or "comprises" are to be interpreted as including the stated integer or integers without necessarily excluding any other integers.

It is to be understood that the terminology employed above is for the purpose of description and should not be regarded as limiting. The described embodiments are intended to be illustrative of the invention, without limiting the scope thereof. The invention is capable of being practised with various modifications and additions as will readily occur to those skilled in the art.

When any number or range is described herein, unless clearly stated otherwise, that number or range is approximate. Recitation of ranges of values herein are intended to serve as a shorthand method of referring individually to each separate value falling within the range, unless otherwise indicated herein, and each separate value and each separate subrange defined by such separate values is incorporated into the specification as if it were individually recited herein.

The invention claimed is:

1. A therapeutic apparatus for an animal, the apparatus comprising:
    a reversible base having a first position where the base has a concave shape with an open top at least partially enclosing a volume, and a plurality of food entrapment members extending from an internal surface of the base into the volume such that the food entrapment members are only accessible from the open top, the food entrapment members and base being made of a food grade material and defining zones in which food can be trapped at least partially inhibiting licking of the food out of the zones, and the base having a second position where the base retains its concave shape and is inverted to present the internal surface and the food entrapment members externally.

2. The apparatus as claimed in claim 1, including a suction device on a side of the base.

3. The apparatus as claimed in 1, in which the food entrapment members are an array of discrete projections.

4. The apparatus as claimed in claim 3, in which the projections are posts or rods that extend from the base, each post or rod being cylindrical and having a rounded upper end.

5. The apparatus as claimed in 1, in which the food entrapment members are each two intersecting catch members which intersect substantially orthogonally.

6. The apparatus as claimed in 1, in which the food entrapment members define an array of discrete pockets in which the food paste can be trapped.

7. The apparatus as claimed in 1, in which the entrapment members are in the form of intersecting ridges.

8. A therapeutic apparatus for an animal, the apparatus comprising:
    a part-ellipsoidal base having a first position that provides an unstable bearing surface and defines and at least partially encloses a volume; and
    a plurality of food entrapment members that extend from an internal surface of the base into the volume such that the food entrapment members are only accessible from a mouth of the base, the food entrapment members and the base are made of a food grade material and define zones in which food can be trapped at least partially inhibiting licking the food out of the zones, the base having a second position where the base retains its shape and is inverted to present the internal surface and the food entrapment members externally.

9. The apparatus as claimed in claim 8, including a suction device on a side of the base.

10. The apparatus as claimed in claim 8, in which the food entrapment members are an array of discrete projections.

11. The apparatus as claimed in claim 8, in which the projections are posts or rods that extend from the base, each post or rod being cylindrical and having a rounded upper end.

12. The apparatus as claimed in claim 8, in which the food entrapment members are each two intersecting catch members which intersect substantially orthogonally.

13. The apparatus as claimed in claim 8, in which the food entrapment members define an array of discrete pockets in which the food paste can be trapped.

14. The apparatus as claimed in claim 8, wherein the base is made of a resilient material.

15. A therapeutic apparatus for an animal, the apparatus comprising:
 a base having a first position that provides an unstable bearing surface that defines and at least partially encloses a volume; and
 a plurality of food entrapment members that extend from an internal surface of the base into the volume such that the food entrapment members are only accessible from a mouth of the base, the food entrapment members and the base are made of a food grade material and define zones in which food can be trapped at least partially inhibiting licking the food out of the zones, the base having a second position where the base retains its shape and is inverted to present the internal surface and the food entrapment members externally.

16. The apparatus as claimed in claim 15, including a suction device on a side of the base.

17. The apparatus as claimed in claim 15, in which the food entrapment members are an array of discrete projections.

18. The apparatus as claimed in claim 15, in which the projections are posts or rods that extend from the base, each post or rod being cylindrical and having a rounded upper end.

19. The apparatus as claimed in claim 15, in which the food entrapment members are each two intersecting catch members which intersect substantially orthogonally.

20. The apparatus as claimed in claim 15, in which the food entrapment members define an array of discrete pockets in which the food paste can be trapped.

21. The apparatus as claimed in claim 15, wherein the base is made of a resilient material.

\* \* \* \* \*